US009022651B2

(12) United States Patent
Kaercher et al.

(10) Patent No.: US 9,022,651 B2
(45) Date of Patent: May 5, 2015

(54) X-RAY DIFFRACTION-BASED DEFECTIVE PIXEL CORRECTION METHOD USING AN ACTIVE PIXEL ARRAY SENSOR

(71) Applicant: Bruker AXS, Inc., Madison, WI (US)

(72) Inventors: Joerg Kaercher, Madison, WI (US); John L. Chambers, Woodville, OH (US)

(*) Notice: Subject to any disclaimer, the term of this patent is extended or adjusted under 35 U.S.C. 154(b) by 117 days.

(21) Appl. No.: 13/940,996

(22) Filed: Jul. 12, 2013

(65) Prior Publication Data

US 2015/0016594 A1 Jan. 15, 2015

(51) Int. Cl.
*G01N 23/207* (2006.01)
*G01N 23/20* (2006.01)
*G01D 18/00* (2006.01)
*G01T 7/00* (2006.01)

(52) U.S. Cl.
CPC ....................................... *G01T 7/005* (2013.01)

(58) Field of Classification Search
USPC ............................... 378/70–78, 204, 207, 210
See application file for complete search history.

(56) References Cited

U.S. PATENT DOCUMENTS

| 7,136,454 | B2 | 11/2006 | Gerndt et al. |
| 2011/0063469 | A1 | 3/2011 | Omi et al. |
| 2013/0108021 | A1 | 5/2013 | Durst et al. |

OTHER PUBLICATIONS

Kabsch, Wolfgang, Evaluation of Single-Crystal X-ray Diffraction Data from a Position-Sensitive Detector, J. Appl. Cryst. (1988), 21, 916-924.
Leslie, A. G. W., Integration of Macromolecular Diffraction Data, Acta Cryst. (1999), D55, 1696-1702.
Duisenberg, Albert J. M., et al., An intensity evaluation method: EVAL-14, J. Appl. Cryst. (2003), 36, 220-229.

*Primary Examiner* — Anastasia Midkiff
(74) *Attorney, Agent, or Firm* — Robic, LLP

(57) ABSTRACT

A method for correcting erroneous intensity measurements caused by defective pixels of the detector for a single-crystal X-ray diffraction system uses collected diffraction images and a defective pixel list to modify three-dimensional reflection profiles by replacing profile elements affected by the defective pixels with corresponding profile elements from a model profile. Reflection positions on the detector are predicted using an orientation matrix for the crystal and a three-dimensional observed profile is constructed for each reflection. A model profile is constructed using normalized profile data from multiple reflection profiles. The observed profiles are compared with the defective pixel list to determine which profile elements are affected by defective pixels, and those elements are replaced by corresponding elements from the model profile. If the replaced elements represent more than a predetermined percentage of the overall reflection intensity, the data for that reflection is omitted from an overall dataset for the crystal.

18 Claims, 3 Drawing Sheets

X-RAY DIFFRACTION-BASED DEFECTIVE PIXEL CORRECTION METHOD USING AN ACTIVE PIXEL ARRAY SENSOR

BACKGROUND OF THE INVENTION

1. Field of the Invention

This invention relates generally to the field of X-ray diffraction and, more specifically, to the analysis of single-crystal specimen using an active pixel array sensor.

2. Description of the Related Art

Single-crystal X-ray diffraction (SC-XRD) is a method for determining the three-dimensional atomic structure of a crystalline compound. A single-crystal specimen of the compound is irradiated with monochromatic X-ray radiation from different directions, some of which is diffracted in specific patterns and detected by an active pixel sensor. The structural information of the specimen is determined from the geometry and relative intensities of these diffraction patterns. The intensities are integrated from the pixels in the active pixel array sensor images.

A typical laboratory system 100 for performing single-crystal diffraction experiments normally consists of five components as shown in FIG. 1. The components include an X-ray source 102 that produces a primary X-ray beam 104 with the required radiation energy, focal spot size and intensity. X-ray optics 106 are provided to condition the primary X-ray beam 104 to a conditioned, or incident, beam 108 with the required wavelength, beam focus size, beam profile and divergence. A goniometer 110 is used to establish and manipulate geometric relationships between the incident X-ray beam 108, the crystal sample 112 and the X-ray sensor 114. The incident X-ray beam 108 strikes the crystal sample 112 and produces scattered X-rays 116 which are recorded in the sensor 114. A sample alignment and monitor assembly comprises a sample illuminator 118 that illuminates the sample 112 and a sample monitor 120, typically a video camera, which generates a video image of the sample to assist users in positioning the sample in the instrument center and monitoring the sample state and position.

The goniometer 110 allows the crystal sample 112 to be rotated around several axes. Precise crystallography requires that the sample crystal 112 be aligned to the center of the goniometer 110 and maintained in that center when rotated around the goniometer rotational axes during data collection. During exposure, the sample (a single crystal of the compound of interest) is rotated in the X-ray beam 108 through a precise angular range with a precise angular velocity. The purpose of this rotation is to predictably bring Bragg reflections into constructive interference with the incident beam 108. During this time, called the charge integration time, the pixels of the sensor receive and integrate the X-ray signals.

Active pixel array sensors used in SC-XRD may include CMOS or CCD imagers. While effective, sensors such as these are often subject to pixel defects. The affected pixels may be permanently dark (i.e., "dead pixels"), permanently bright (i.e., "hot pixels"), or they may exhibit other behavior that prevents an accurate signal from being detected at these pixel locations. As such, to maintain an accurate signal detection, diffraction intensities that overlap with defective pixels must either be rejected, or estimated values must be in place of a useful response from the defective pixels.

Most established methods for pixel defect correction use nearby good pixels to determine replacement pixel values. In the simplest case, the replacement pixel value is copied from one of the neighboring pixels. More sophisticated approaches use linear or higher order interpolation across neighbors on both sides of the defective pixels and in one or two dimensions. In most cases the corrected pixel values are good enough to be inconspicuous to the human eye but, in the case of single-crystal X-ray diffraction images, they seldom pass the scrutiny of a numerical analysis. The affected intensities are often trapped as outliers and need to be rejected from the data. Moreover, if they remain undetected, they can negatively influence the result of the structure analysis.

SUMMARY OF THE INVENTION

In accordance with the present invention, a method is provided for correcting erroneous intensity measurements caused by defective pixels of the detector of a single-crystal X-ray diffraction system in which diffraction images are collected from a plurality of different scan angles for a crystal mounted in the system. From the diffraction images, reflection positions on the detector are predicted using an orientation matrix established for the crystal. A three-dimensional observed profile is then constructed for each reflection. This profile is indicative of pixel intensity relative to scan angle for detector pixels falling within the predicted reflection position on the detector. A learned "model" profile is also constructed as an average of the normalized profile data from a plurality of reflection profiles, and a defective pixel list for the system is provided that is indicative of the location of defective pixels in the detector. For each reflection under examination, the defective pixel list is then compared with the observed profile for that reflection to determine components of that observed profile that are affected by a defective pixel, and those components are replaced with corresponding components from the model profile.

The method may also involve the step of rejecting a reflection from the system output data if too much of the reflection data is affected by one or more defective pixels. In such a case, after replacing components of an observed profile with corresponding components from the model profile, a determination is made as to what percentage of an overall intensity represented by that observed profile is attributable to the components that were replaced. If that percentage exceeds a predetermined value, the reflection is then omitted from the output data. The exact percentage may vary depending on the application but, in an exemplary embodiment, a value of twenty-five percent is used.

In one embodiment, the model profile is updated during the correction process. In this embodiment, when a reflection under examination is found to have no components that are affected by a defective pixel, a determination is made as to whether the reflection is a "strong" reflection, that is, whether it has an intensity above a certain threshold. If so, the data from that reflection is used to update the model profile.

The invention also encompasses variations on how to construct the model profile. In one embodiment, the model profile is constructed using data from substantially all of the observed profiles for reflections having a minimum intensity. In an alternative embodiment, however, a different model profile is constructed for each of the reflections. In this embodiment, the detector surface is divided into a predetermined number of different detection regions, and the model profile for a given reflection comprises a weighted average of normalized data from a plurality of regional model profiles, each of which is associated with a different one of the detector regions and each of which is constructed as an average of the normalized profile data from observed profiles of reflections falling within its respective detector region. In an exemplary embodiment, there are nine detector regions, each having the same area, although a different number of detector regions and relative sizes may also be used. The calculation of the weighted average of the regional profile data may also vary depending on the application. For example, the weighted average may be such that the data from a given regional profile is weighted as a function of the distance from a predicted centroid of the reflection to a center of the region with which that regional profile is associated.

A method according to the present invention may also include the determination of an integrated intensity value for each reflection by calculating a summation of components of the observed profile for that reflection. Different methods of making this determination are anticipated herein and, in one embodiment, the integrated intensity value for a given reflection includes calculating a weighted sum of components of the observed profile for that reflection and the corresponding components of the model profile. However, other methods may also be used.

DETAILED DESCRIPTION

Figure 1:
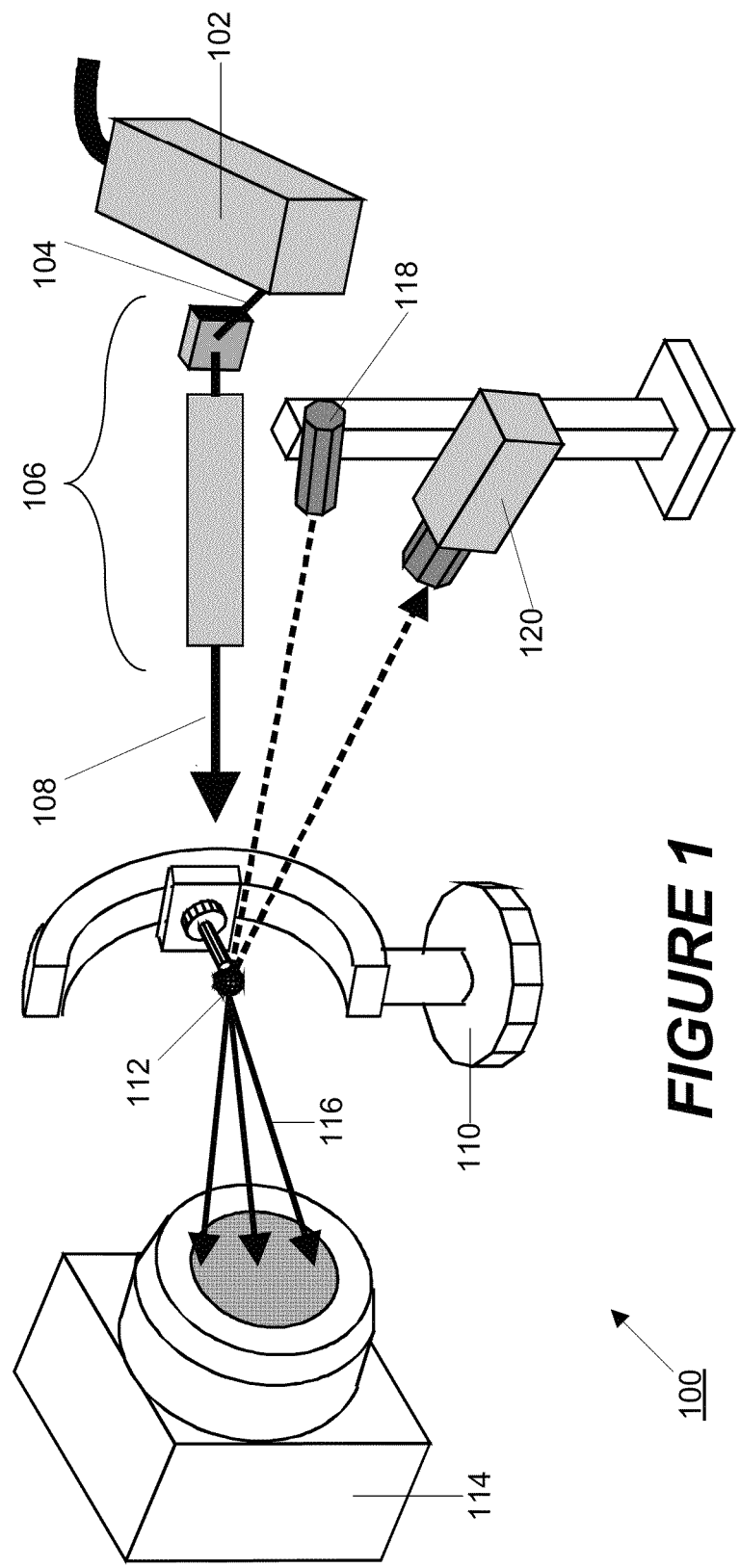
FIG. 1 is a schematic view of a single-crystal X-ray diffraction analysis system according to the prior art.

The present invention provides a correction of errors resulting from defective pixels in the active pixel array sensor of a single-crystal X-ray diffraction system. The steps of a method according to an exemplary embodiment of the invention are shown in the flow diagram of FIG. 2. In step 200, the diffraction images collected during the examination of a single-crystal sample with an instrument such as that shown in FIG. 1 are input. The number of images depends on the specific instrument and experiment in question. For example, the images may be collected from three or four different "runs" of the system, with the crystal being rotated about a different axis during each run. For each run, many different images are collected, an example being the capturing of one image for each 0.5 degrees of rotation during an overall rotation of 180 degrees. The different number of runs and the angles depend on factors specific to the experiment, such as the symmetry of the crystal, and are chosen in a manner known in the art as is necessary to obtain a full representation of the crystal.

Using the data from the images, the positions of the reflections on the detector surface may be predicted (step 202) using the orientation matrix and other data, such as the location of the detector and its angular orientation. The determination of an orientation matrix is known in the art, and provides information regarding the orientation of the crystal and the geometry of its lattice. Thus, a set of predictions is made so that, for different scan angles, the expected location of a reflection on the detector, and therefore which pixels will be illuminated by the reflection, is identified.

Figure 2:
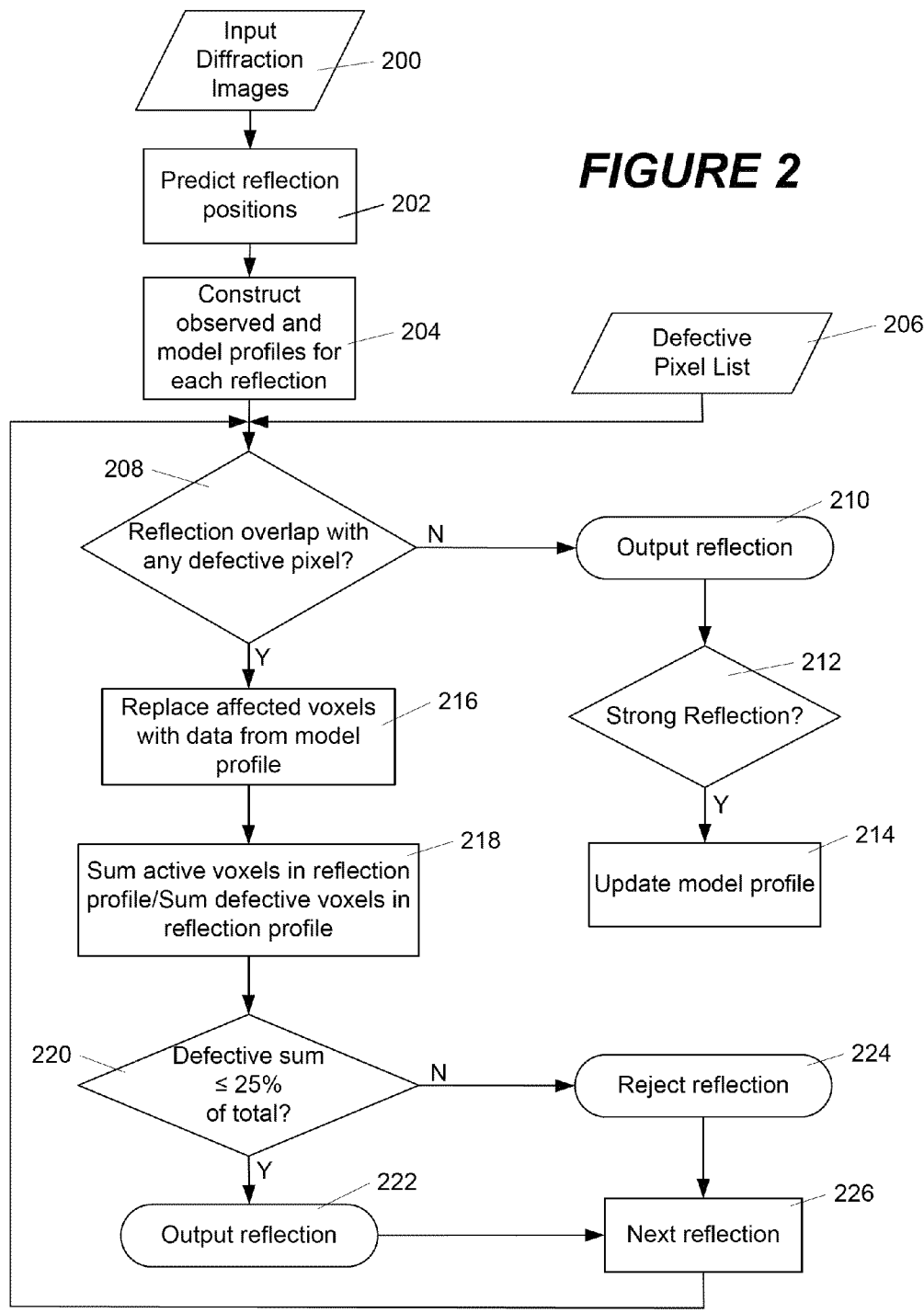
FIG. 2 is a flow diagram showing the steps according to an exemplary embodiment of the invention.

In step 204 of FIG. 2, an "observed profile" is constructed for each reflection. A common type of reflection profile known in the art is referred to as a "Kabsch profile," and is described in: Wolfgang Kabsch, *J. Appl. Cryst.* (1988) 21, 916-924. Such a profile is a three-dimensional dataset that represents a reflection in two spatial dimensions with a third dimension representing scan angle. Thus, a profile is made up of grid points, or "voxels" that are indicative of the intensity distribution of the reflection over a finite number of scan angles, and each voxel may be identified by coordinates X, Y and Z, where X and Y are in the image plane, and Z is the scan direction through the image plane. In this coordinate system, each reflection profile appears as if it were acquired by the shortest path through the Ewald sphere, and thus the shapes of the profiles are similar throughout reciprocal space.

In order to minimize sampling error, a convolver is applied to each background-subtracted image pixel before distributing its intensity over the profile grid points within the range of the convolver. The optimal convolver size is determined from the relative sizes of the XYZ pixels in image space versus the grid size in profile space. However, when an image pixel is entered into a profile, its intensity is conserved. That is, the sum of the profile values increases by exactly the value of the image pixel, although the pixel may contribute to several profile points. By default, the size of a profile in the present embodiment is 9×9×9, although those skilled in the art will understand that other magnitudes may also be chosen.

In addition to the observed reflection profiles, a normalized learned "model" profile for a specific reflection is computed as a weighted average of a number of different observed profiles. For example, in a first embodiment, there is a single model profile that is constructed using all of the shape-adjusted observed profiles of strong reflections, i.e., reflections having an intensity above a particular magnitude. Thus, for each of these strong reflections, the observed profile data is adjusted spatially to account for any shape variations relative to the other reflection profiles, and is normalized and averaged with the profile data of the other reflections. In this way, the model profile represents an average intensity distribution (in the three-dimensional profile space) of all of the reflections. This model profile will be used subsequently to correct for profile data of specific observed reflection profiles that have been compromised by one or more defective pixels.

In an alternative embodiment, multiple model profiles may be constructed relative to different regions of the detector. For example, the detector surface may be divided into nine different regions of equal area, and a model profile constructed for each of the regions, although those skilled in the art will recognize that different numbers of detector regions may also be chosen. These regional model profiles are constructed in the same manner as for the single model profile embodiment discussed above, except that each uses only reflection data that originates in the region of the detector that it represents. The model profiles are used for replacing voxels of specific observed reflection profiles that are compromised by defective pixels but, for a given reflection, the normalized model profile used is calculated as a weighted average of normalized model profiles from the different detector regions, where the weight is a function of the distance from the predicted reflection centroid to the center of each region.

In each of the aforementioned embodiments, the model profile may be constructed during an initial run prior to the process of correcting the reflection data. However, as discussed below, the model profile may also be modified during the process of collecting the reflection data and doing the correction. In such a case, the model profile would typically start as an ideal Gaussian profile and, before the main integration starts, a number of preliminary integration passes would be conducted to "seed" the model profile with information. Then, during the subsequent integration and pixel correction steps, the model profile is improved by adding data from strong reflections that are uncompromised by the influence of defective pixels.

For doing pixel correction according to the present invention, the observed profile for a given reflection is used together with a defective pixel list that is built from tests applied to the detector itself. These tests are conducted prior to any crystal examination, and may be part of the factory calibration process. Methods for finding defective pixels are known in the art. One method involves exposing the entire detector and taking a series of images of increasing intensity to the point of approaching saturation. An intensity curve is then fit to each pixel to find which of them has a defective response.

Referring again to FIG. 2, the defective pixel list is provided (step 206) along with the observed profile for a first reflection (step 204), and a determination is made as to whether the reflection overlaps with any of the defective pixels (step 208). If not, the reflection is output (step 210) and a determination is made as to whether this is particularly strong reflection (step 212). If so, this may be used to update the model profile (step 214), as a strong reflection (i.e., above a certain threshold) provides valuable data that may be relevant to the other reflections.

If the reflection being examined overlaps with any defective pixels, the voxels that are affected are replaced with data from the model profile (step 216), either as originally built, or as updated in step 214. The model profile may be derived from all of the observed reflection profile data, or it may be based on a weighted average of multiple model profiles from different detector regions, as discussed above.

After replacing the affected voxels in the observed reflection profile, a determination is made as to what percentage of the intensity was considered to be "defective" due to the influence of a defective pixel. The total intensity from all voxels and the intensity from all defective voxels are summed, respectively (step 218), and if the total intensity of defective voxels is less than or equal to 25% of the total intensity of voxels in that learned model profile (step 220), the reflection is output (step 222). If the total intensity of defective voxels is greater than 25%, the reflection is rejected (step 224). The method then proceeds to the observed profile for the next reflection (step 226), and the evaluation process recommences.

Figure 3:
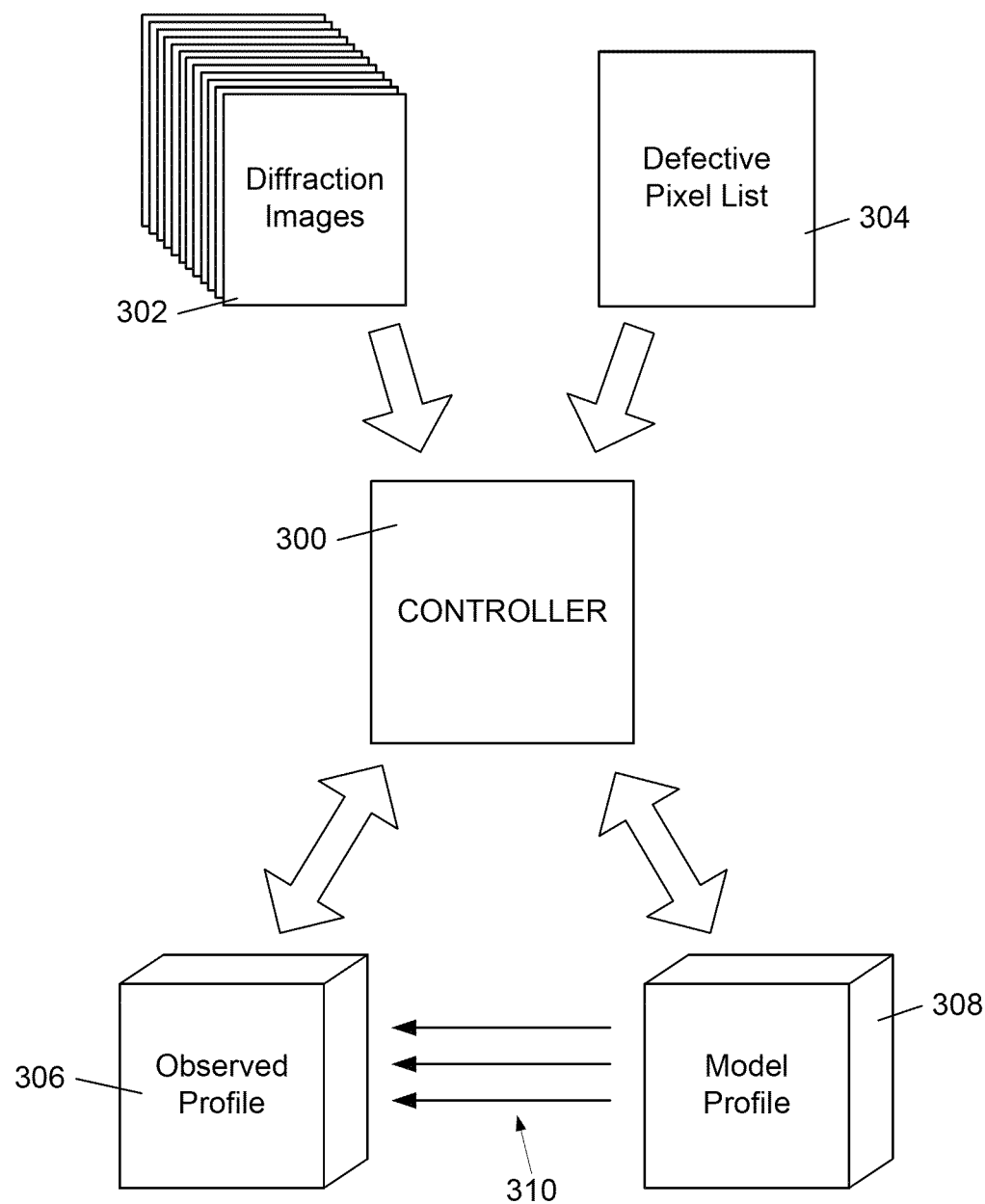
FIG. 3 is a schematic diagram showing the elements of a system according to the present invention.

FIG. 3 provides a schematic overview of the process according to the invention. While this graphical depiction shows the different elements that are used to create a corrected observed reflection profile, it will be understood that the order of the process is as discussed above with regard to FIG. 2. As shown, a controller 300, which may be, for example, a computer or dedicated data processor, receives the data from the diffraction images 302 gathered from the crystal under examination, and also has as an input the defective pixel list 304 for the system detector. For each reflection, the controller 300 constructs the observed reflection profile 306 as discussed above. The model profile 308 is also constructed and updated by the controller 300 when there is strong reflection data available that is not compromised by defective pixels. Also represented schematically in the drawing are components 310 of the model profile that are used to replace corresponding components of the reflection profile due to the reflection profile components being compromised by defective pixel data. Finally, as indicated by the double-headed arrows between the controller 300 and each of the observed profile 306 and the model profile 308, data from the observed profile, and possibly the model profile, may be used during integration of the reflection.

In the present embodiment, reflections are integrated using data from the observed profiles of the reflections, including voxels that have been replaced to compensate for the effect of a defective pixel. Before starting integration, a user enters estimates of the size in X, Y and Z of a "nominal" spot. These size estimates are used to define an ellipsoid around each predicted spot position to define the volume (a parallelepiped, referred to as the "integration box") over which observed reflection profiles are accumulated. Input X, Y and Z size estimates are typically refined in preliminary passes through the first few images before integration.

The integrated intensity is determined for every reflection profile by two different techniques: simple summation and least-squares (LS) profile fitting. In both cases, the summation volume used, that is the voxels that will be included in the summation, is determined from the observed profile. In particular, a cross-section of the observed profile having an intensity at a certain minimum percentage of that of the profile peak intensity (4% in the present embodiment) serves as the footprint for the reflection, i.e., the area on the detector from which pixels are summed. From this the voxels that correspond to this detector area may be determined, and are considered to make up the summation volume. In the case of simple summation, the integrated intensity is computed by summing those pixels in the reflection's observed profile that lie within the summation volume. By using the inverse of the operation described above for populating the voxels in the observed profile with pixel intensities it is possible to go from "profile space" back to "detector space" to find the relevant detector pixels. In the case of LS fitting, the integration is also over the summation volume, but the LS-fit intensity involves a weighted sum of the observed profile and the model profile at the reflection's centroid position. That is, the footprint is determined as described above, but instead of simply summing the pixels inside this footprint, the model profile is scaled to best fit the intensities of the pixels inside the footprint, and the voxel intensities of that scaled profile are then summed to form the "LS-fit intensity." The final integrated intensity is then determined as a weighted sum of the LS-fit intensity and the simple summation.

Those skilled in the art will understand that the steps of the different embodiments of the invention described herein will typically be performed by a data processor as part of a sampling and data collection procedure. Thus, once the system is set up with the desired criteria, and a sample crystal properly located therein, the system can typically perform the data collection and integration process without the need for manual intervention by a user.

What is claimed is:

1. A method of correcting erroneous intensity measurements caused by defective pixels of the detector of a single-crystal X-ray diffraction system during the collection of diffraction images from a plurality of different scan angles for a crystal mounted in the system, the method comprising the steps of:
   a) predicting reflection positions on the detector from the diffraction images using an orientation matrix established for the crystal;
   b) constructing a three-dimensional observed profile for each reflection, said observed profile being indicative of pixel intensity relative to scan angle for detector pixels falling within a predicted reflection position as determined in step (a);
   c) constructing a model profile as an average of the normalized profile data from a plurality of observed profiles;
   d) providing a defective pixel list for the system indicative of the location of defective pixels in the detector; and
   e) for each reflection under examination, comparing the defective pixel list with the observed profile for that reflection to determine components of that observed profile that are affected by a defective pixel, and replacing said components with corresponding components from the model profile.

2. A method according to claim 1 wherein, for a reflection having no components that are affected by a defective pixel, the method further comprises determining whether said reflection has an intensity above a certain threshold and, if so, using the data from that reflection to update the model profile.

3. A method according to claim 1 further comprising, after replacing the components of an observed profile in step (e), determining the percentage of an overall intensity represented by that observed profile that is attributable to the components that were replaced and, if said percentage exceeds a predetermined value, omitting the reflection from the system output data.

4. A method according to claim 3 wherein said predetermined value is twenty-five percent.

5. A method according to claim 1 wherein the model profile is constructed using data from substantially all of the observed profiles for reflections having a minimum intensity.

6. A method according to claim 1 wherein a different model profile is constructed for each of the reflections.

7. A method according to claim 6 wherein the detector is divided into a predetermined number of different detection regions, and the model profile for a given reflection comprises a weighted average of normalized data from a plurality of regional profiles, each of which is associated with a different one of said detector regions, and each of which is constructed as an average of the normalized profile data from observed profiles of reflections falling within its respective detector region.

8. A method according to claim 7 wherein the weighted average is such that the data from a given regional profile is weighted as a function of the distance from a predicted centroid of the reflection to a center of the region with which that regional profile is associated.

9. A method according to claim 7 wherein each of the regions comprises substantially the same area on the detector surface.

10. A method according to claim 7 wherein said predetermined number of detector regions is nine.

11. A method according to claim 1 further comprising determining an integrated intensity value for each reflection by calculating a summation of components of the observed profile for that reflection.

12. A method according to claim 11 wherein the components included in the summation are those components that correspond to detector pixels that register an intensity that is no less than a predetermined percentage of the maximum intensity measured by any detector pixel for that reflection.

13. A method according to claim 12 wherein the predetermined percentage is four percent.

14. A method according to claim 12 wherein said components included in the summation are a first set of components, and wherein determining the integrated intensity for a given reflection further comprises calculating a weighted sum of the first set of components and a corresponding set of components of the model profile.

15. A method of correcting erroneous intensity measurements caused by defective pixels of the detector of a single-crystal X-ray diffraction system during the collection of diffraction images from a plurality of different scan angles for a crystal mounted in the system, the method comprising the steps of:

a) predicting reflection positions on the detector from the diffraction images using an orientation matrix established for the crystal;
b) constructing a three-dimensional observed profile for each reflection, said observed profile being indicative of pixel intensity relative to scan angle for detector pixels falling within a predicted reflection position as determined in step (a);
c) constructing a model profile as an average of the normalized profile data from a plurality of observed profiles;
d) providing a defective pixel list for the system indicative of the location of defective pixels in the detector;
e) for each reflection under examination, comparing the defective pixel list with the observed profile for that reflection to determine components of that profile that are affected by a defective pixel, and replacing said components with corresponding components from the model profile; and
f) for each reflection having profile components in step (e) determining an overall intensity represented by the observed profile for that reflection that is attributable to the components that were replaced and, if said percentage exceeds a predetermined value, omitting data collected for that reflection from an overall dataset collected by the system for the crystal.

16. A method according to claim 15 wherein said predetermined value is twenty-five percent.

17. A method according to claim 15 wherein, for a reflection having no components that are affected by a defective pixel, the method further comprises determining whether said reflection has an intensity above a certain threshold and, if so, using the data from that reflection to update the model profile.

18. A method of correcting erroneous intensity measurements caused by defective pixels of the detector of a single-crystal X-ray diffraction system during the collection of diffraction images from a plurality of different scan angles for a crystal mounted in the system, the method comprising the steps of:

a) predicting reflection positions on the detector from the diffraction images using an orientation matrix established for the crystal;
b) constructing a three-dimensional observed profile for each reflection, said observed profile being indicative of pixel intensity relative to scan angle for detector pixels falling within a predicted reflection position as determined in step (a);
c) constructing a model profile as an average of the normalized profile data from a plurality of reflection profiles;
d) providing a defective pixel list for the system indicative of the location of defective pixels in the detector;
e) for each reflection under examination, comparing the defective pixel list with the observed profile for that reflection to determine components of that observed profile that are affected by a defective pixel, and replacing said components with corresponding components from the model profile; and
f) for each reflection under examination that has no components that are affected by a defective pixel, determining whether said reflection has an intensity above a certain threshold and, if so, using the data from that reflection to update the model profile.

* * * * *